(12) United States Patent
Grueebler et al.

(10) Patent No.: US 10,675,390 B2
(45) Date of Patent: Jun. 9, 2020

(54) COMBINED COAXIAL AND BIMANUAL IRRIGATION/ASPIRATION APPARATUS

(71) Applicant: Alcon Inc., Fribourg (CH)

(72) Inventors: Reto Grueebler, Greifensee (CH); Stephen Lane, Shoreview, MN (US); Philipp Schaller, Stein am Rhein (CH)

(73) Assignee: Alcon Inc., Fribourg (CH)

( * ) Notice: Subject to any disclaimer, the term of this patent is extended or adjusted under 35 U.S.C. 154(b) by 36 days.

(21) Appl. No.: 15/225,953

(22) Filed: Aug. 2, 2016

(65) Prior Publication Data

US 2016/0339157 A1 Nov. 24, 2016

Related U.S. Application Data

(63) Continuation of application No. 13/686,430, filed on Nov. 27, 2012, now Pat. No. 9,433,725.

(60) Provisional application No. 61/579,774, filed on Dec. 23, 2011.

(51) Int. Cl.
*A61M 1/00* (2006.01)
*A61M 3/02* (2006.01)
*A61F 9/007* (2006.01)

(52) U.S. Cl.
CPC ....... *A61M 1/0064* (2013.01); *A61F 9/00736* (2013.01); *A61M 1/008* (2013.01); *A61M 3/0283* (2013.01); *A61M 2210/0612* (2013.01)

(58) Field of Classification Search
CPC A61F 9/00736; A61M 1/0064; A61M 3/0283
See application file for complete search history.

(56) References Cited

U.S. PATENT DOCUMENTS 3,882,872 A * 5/1975 Douvas ................. A61B 17/32
606/107
2007/0244425 A1 * 10/2007 Pond .................. A61C 17/0208
604/27

\* cited by examiner

*Primary Examiner* — Deanna K Hall

(57) ABSTRACT

A hand piece having an irrigation portion and an aspiration portion that are releasably coupled is disclosed. In an assembled configuration, the irrigation portion and the aspiration portion are coupled such that the hand piece may be manipulable by a user as a single unit. In a separated configuration, the irrigation portion and the aspiration portion may be utilized separate from each other. The irrigation portion and the aspiration portion may be freely moved between the assembled configuration and the separated configuration.

19 Claims, 9 Drawing Sheets

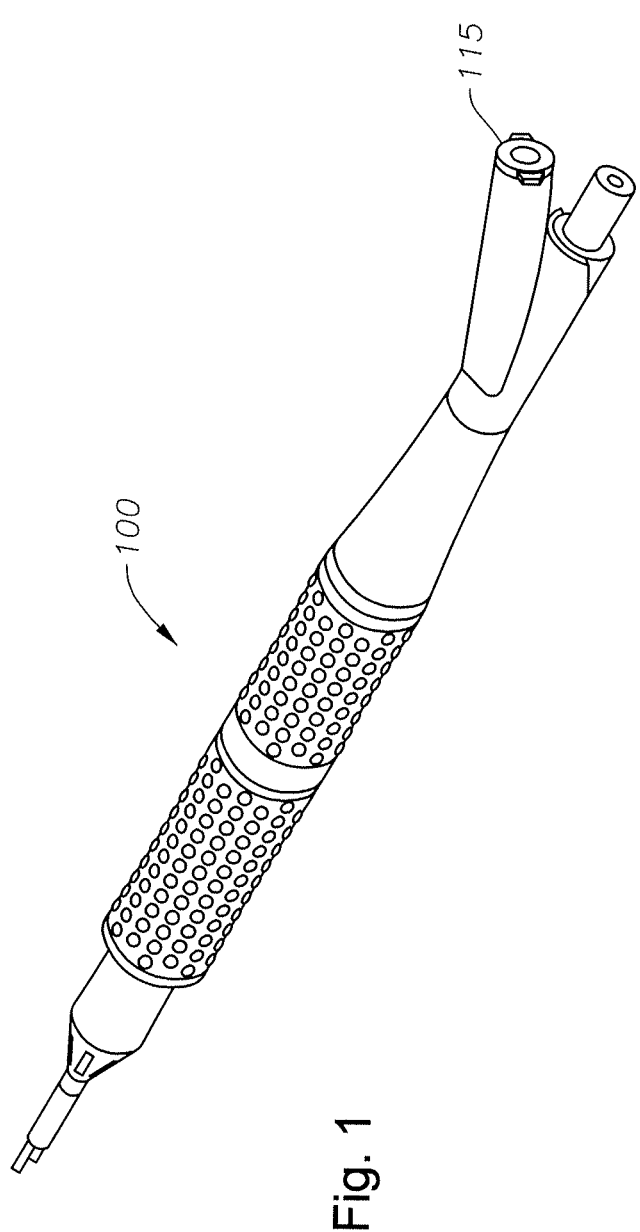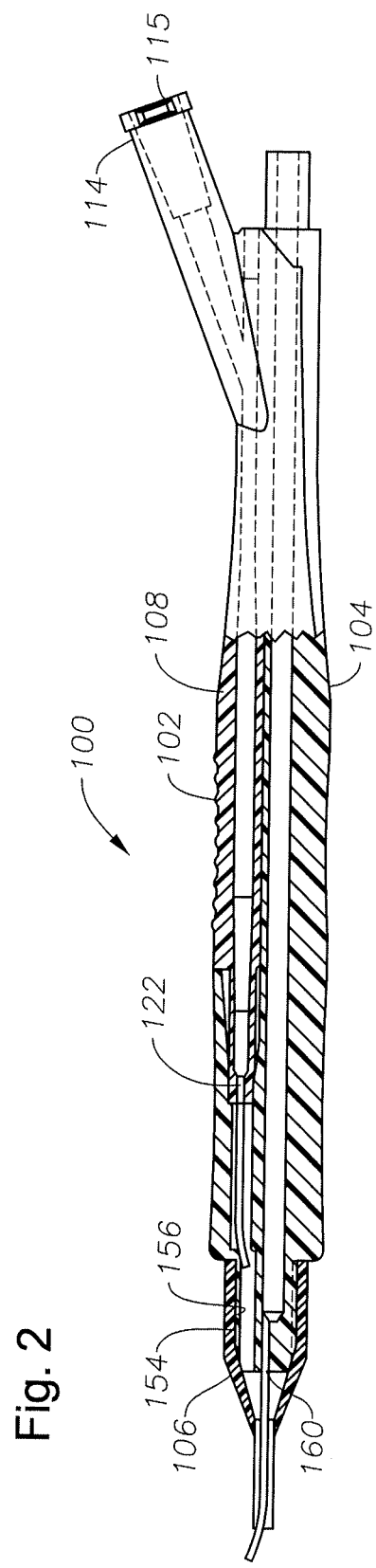

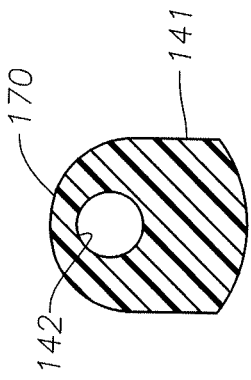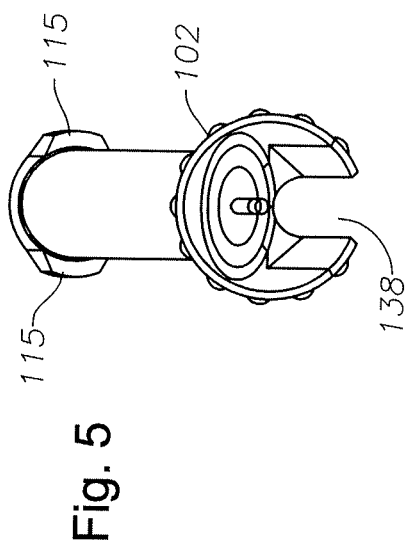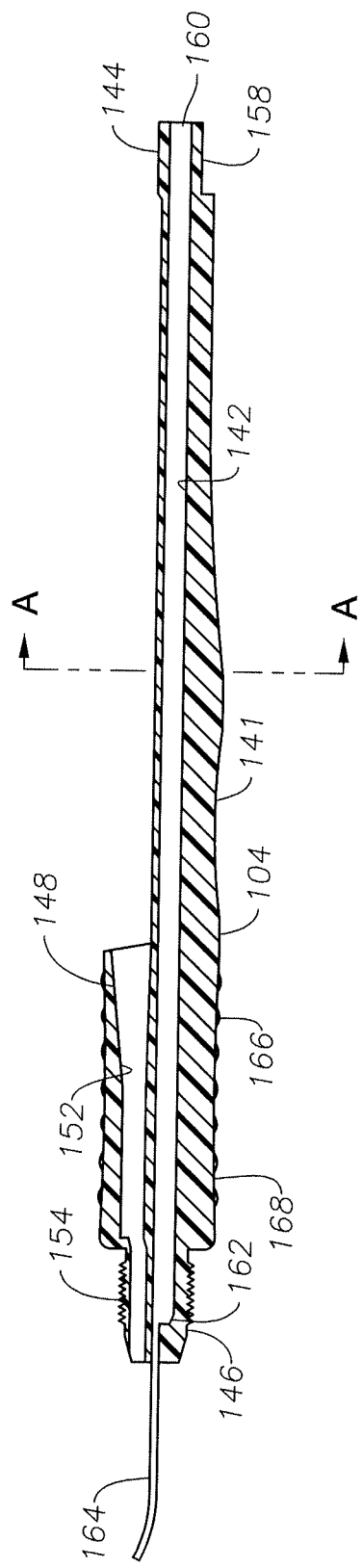

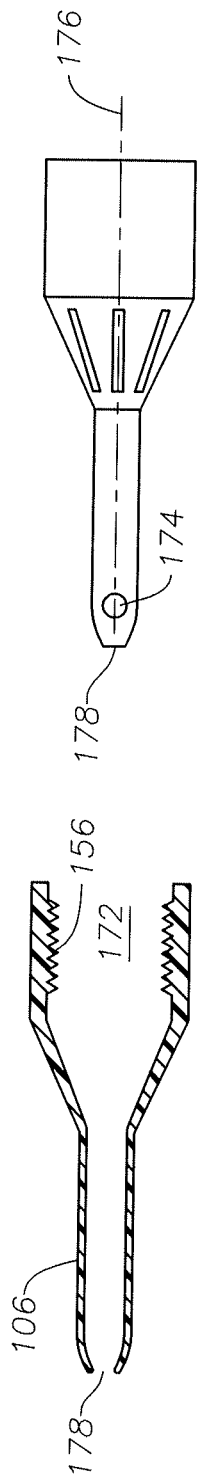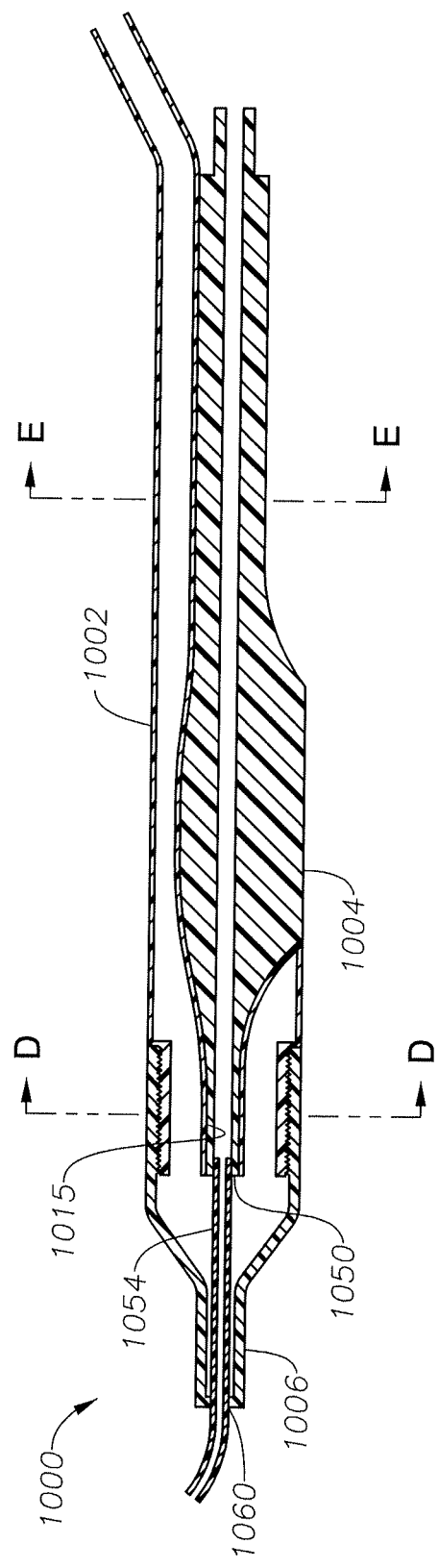
Fig. 8
Fig. 9
Fig. 10

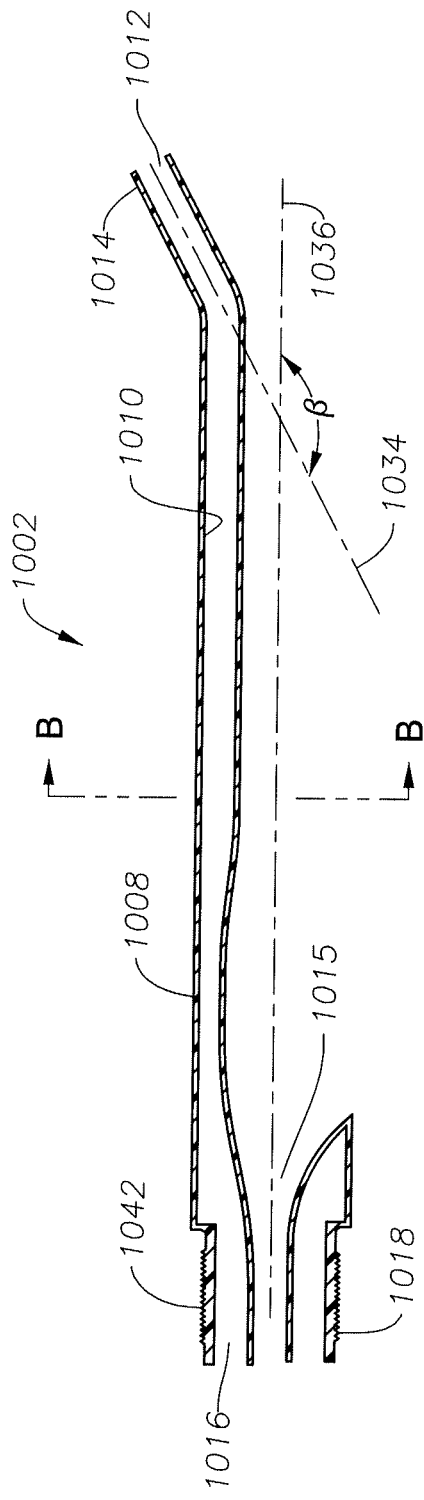
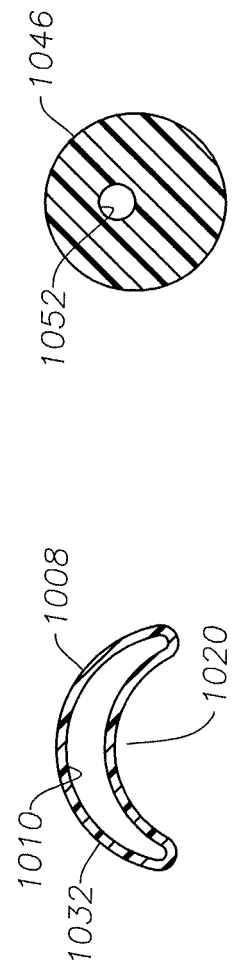
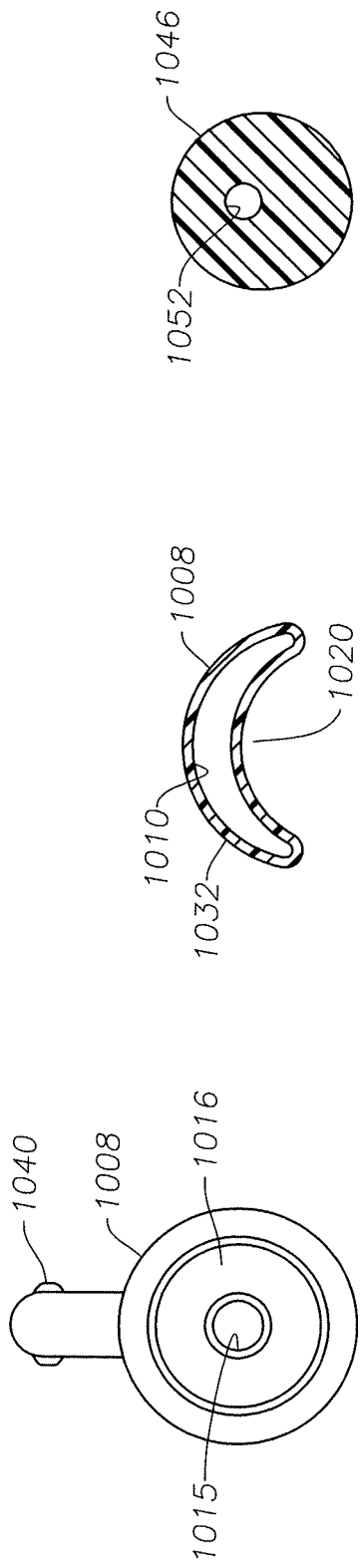

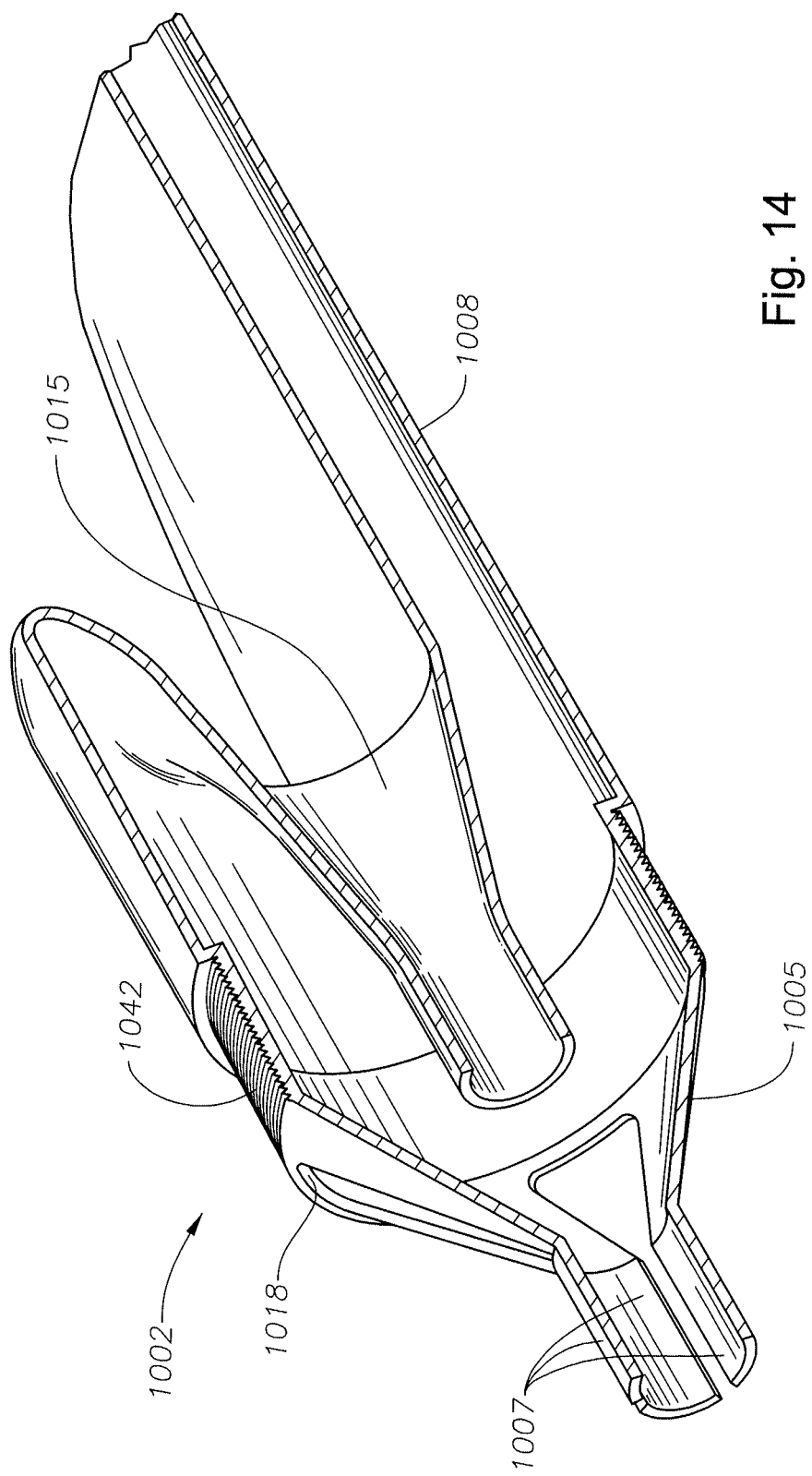

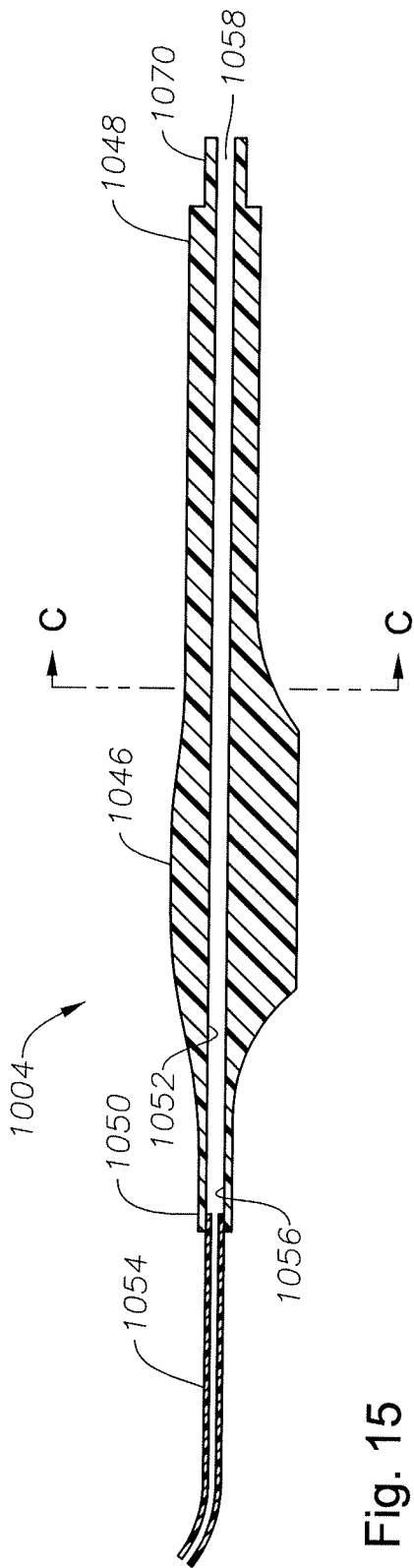
Fig. 15
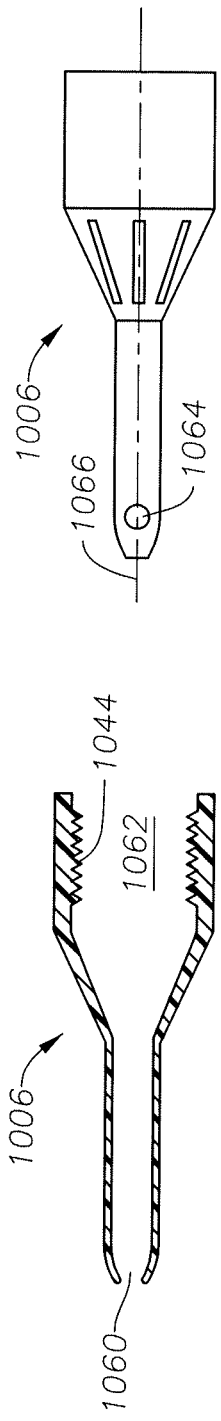
Fig. 17
Fig. 18

COMBINED COAXIAL AND BIMANUAL IRRIGATION/ASPIRATION APPARATUS

CROSS REFERENCE TO RELATED APPLICATIONS

This application is a continuation of U.S. patent application Ser. No. 13/686,430, filed Nov. 27, 2012 and claims the benefit of U.S. Provisional Application No. 61/579,774, filed Dec. 23, 2011, the entire contents of which are incorporated herein by reference.

TECHNICAL FIELD

The present disclosure relates to a surgical hand piece and particularly to an irrigation and aspiration hand piece for use during a surgical procedure.

BACKGROUND

The present disclosure relates generally to a combined coaxial and bimanual irrigation/aspiration ("I/A") surgical instrument used in surgical procedures such as, for example, a phacoemulsification procedure.

The human eye functions to provide vision by transmitting light through a clear outer portion called the cornea, and focusing the image by way of a crystalline lens onto a retina. The quality of the focused image depends on many factors including the size and shape of the eye, and the transparency of the cornea and the lens. When age or disease causes the lens to become less transparent, vision deteriorates because of the diminished light which can be transmitted to the retina. This deficiency in the lens of the eye is medically known as a cataract. An accepted treatment for this condition is surgical removal of the lens and replacement of the lens function by an artificial intraocular lens.

SUMMARY

According to one aspect, the disclosure describes an I/A hand piece that includes an irrigation portion and an aspiration portion. One of the irrigation portion or the aspiration portion may include a receptacle into which a portion of the other of the irrigation portion or the aspiration portion is removably received.

Another aspect of the disclosure encompasses an I/A hand piece that includes an irrigation portion and an aspiration portion. The irrigation portion may include an inlet, and outlet, and a passage extending between the inlet and the outlet. The aspiration portion may include an inlet, an outlet, a passage extending between the inlet and the outlet, and a receptacle. The I/A hand piece may be selectively configured between an assembled configuration in which a portion of the irrigation portion is releasably received into the receptacle of the aspiration portion and a separated configuration in which the irrigation portion and the aspiration portion are decoupled from each other.

The various aspects may include one or more of the following features. One of the irrigation portion or the aspiration portion may include a body defining a recess. The other of the irrigation portion or the aspiration portion may include a body having a profile configured to be releasably received into the recess. The recess may extend longitudinally along the body. The receptacle and the portion of the other of the irrigation portion or the aspiration portion may be received within the receptacle form a fluid-tight seal. The hand piece is selectively configurable between an assembled configuration in which the irrigation portion and the aspiration portion are coupled together such that the at least a portion of irrigation portion or the aspiration portion is received within the receptacle of the other of the irrigation portion or the aspiration portion and a separated configuration in which the irrigation portion and the aspiration portion are decoupled from each other. The hand piece may also include an irrigation sleeve.

Also, the aspiration portion may include the receptacle, and at least a portion of the irrigation portion is may be received within the receptacle in the assembled configuration. The irrigation sleeve may be coupled to a distal end of the aspiration portion. The aspiration portion may include an aspiration needle, and the aspiration needle may extend through an opening formed in the irrigation sleeve. The irrigation portion may include a passage, and the passage of the irrigation portion may communicate with an interior of the irrigation sleeve. A proximal portion of the irrigation sleeve may be releasably coupled to a distal end of the aspiration portion. The irrigation portion may include a longitudinally-extending recess, and the aspiration portion may include a cross-sectional shape configured to be releasably received into the longitudinally-extending recess.

Further, the irrigation portion may include the receptacle, and at least a portion of the aspiration portion may be received within the receptacle in the assembled configuration. The irrigation portion may include an annular outlet formed at a distal end thereof, and the receptacle of the irrigation portion may define a central opening disposed in a central region circumscribed by the annular opening. The aspiration portion may be received in the receptacle. A distal portion of the aspiration portion may extend through the central opening of the irrigation portion. The aspiration portion may include an aspiration needle. The irrigation sleeve may be coupled to a distal end of the irrigation portion, and the aspiration needle may extend through an opening formed in the irrigation sleeve. The irrigation portion may include a longitudinally-extending recess, and the aspiration portion may include a cross-sectional shape configured to be releasably received into the longitudinally-extending recess.

The various aspects may also include one or more of the following features. An inner surface of the receptacle and an outer surface of the irrigation portion may form a fluid-tight seal around the irrigation portion. An irrigation sleeve may be releasably coupled to a distal end of the aspiration portion. The irrigation portion may include an irrigation needle. An outlet of the irrigation needle may be in communication with an interior of the irrigation sleeve. The aspiration portion may include an aspiration needle, and the aspiration needle may extend through an opening formed in the irrigation sleeve. The irrigation portion may include a longitudinally-extending recess, and the aspiration portion may include a cross-sectional shape configured to be releasably received into the longitudinally-extending recess.

The details of one or more implementations of the present disclosure are set forth in the accompanying drawings and the description below. Other features, objects, and advantages will be apparent from the description and drawings, and from the claims.

DESCRIPTION OF THE DRAWINGS

FIG. 1 is a perspective view of an example I/A hand piece.

FIG. 2 is a cross-sectional view of the example I/A hand piece shown in FIG. 1 in an assembled configuration.

FIG. 5 is a front view of example irrigation portion shown in FIG. 3.

FIG. 6 is a cross-sectional view of an example aspiration portion of the example I/A hand piece shown in FIG. 1.

FIG. 7 is a transverse cross-sectional view along line A-A of the example aspiration portion of FIG. 6.

FIG. 8 is a cross-sectional view of an example irrigation sleeve.

FIG. 9 is a side view of the example irrigation sleeve of FIG. 8.

FIG. 10 is a cross-sectional view of another example I/A hand piece in an assembled configuration.

FIG. 11 is a cross-sectional view of an irrigation portion of the example I/A hand piece shown in FIG. 10.

FIG. 12 is front view of the example irrigation portion shown in FIG. 11.

FIG. 13 is a transverse cross-sectional view of the example irrigation portion of FIG. 11 along line B-B.

FIG. 14 is a perspective view of a partial cross-section of another example irrigation portion having stiffening features.

FIG. 15 is a cross-sectional view of an example aspiration portion of the example I/A hand piece of FIG. 10.

FIG. 16 is a transverse cross-sectional view of the example aspiration portion shown in FIG. 15 along line C-C.

FIG. 17 is a cross-sectional view of an example irrigation sleeve.

FIG. 18 is a side view of the example irrigation sleeve of FIG. 16.

DETAILED DESCRIPTION

The present disclosure relates to a surgical instrument for use in a surgical procedure. Particularly, the present disclosure relates to a hand piece operable to perform irrigation and aspiration in the course of a surgical procedure. Particularly, the surgical instrument is an I/A hand piece that is separable into an irrigation portion and an aspiration portion that may be used in a bimanual surgical procedure. In some implementations, the example surgical instruments described herein may be used in ophthalmic surgical procedures and, particularly, in phacoemulsification surgical procedures.

FIGS. 1-9 show an example I/A hand piece 100. The hand piece 100 includes an irrigation portion 102, an aspiration portion 104, and an irrigation sleeve 106. FIG. 2 shows the hand piece 100 in an assembled configuration in which the irrigation portion 102 and the aspiration portion 104 are coupled together. In the assembled configuration, the hand piece 100 provides a single instrument that provides both irrigation and aspiration functionality. Thus, a user, such as, for example, a surgeon or other medical professional, can utilize the hand piece 100 using a single hand, freeing up the user to perform other tasks with the other hand.

Figure 3:
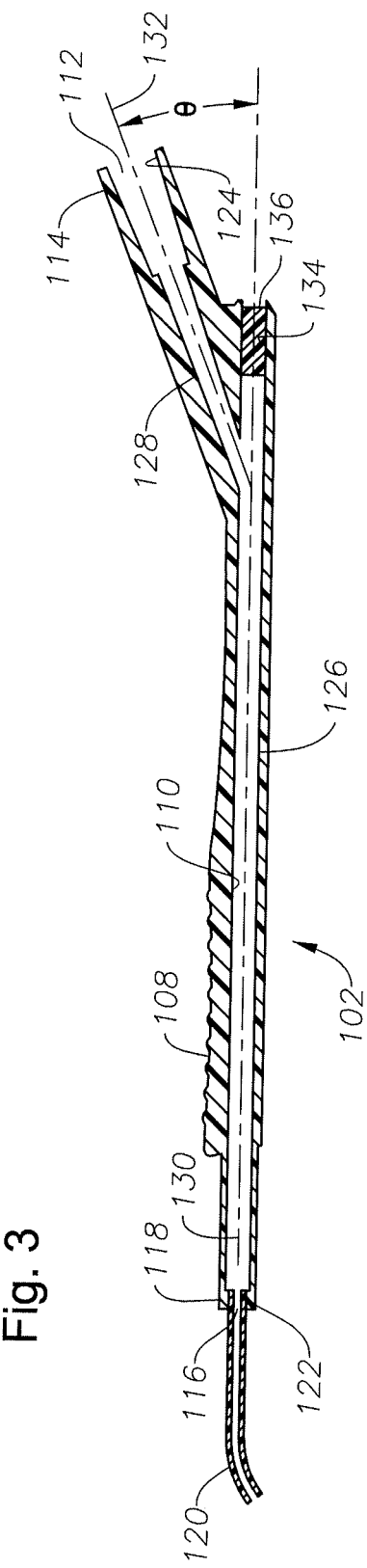
FIG. 3 is a cross-sectional view of an example irrigation portion of the example I/A hand piece shown in FIG. 1.
Figure 4:
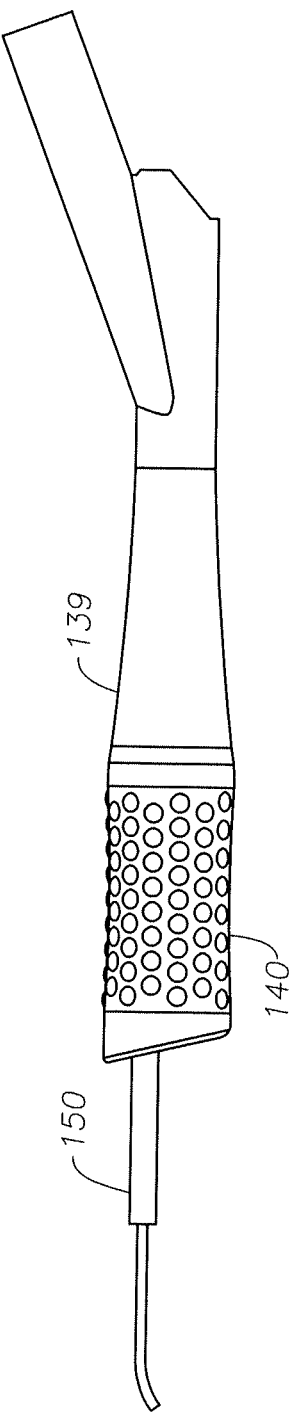
FIG. 4 is a side view of the example irrigation portion shown in FIG. 3.

FIGS. 3-5 show an example irrigation portion 102. FIG. 3 shows a cross-sectional view of the irrigation portion 102. As shown, the irrigation portion 102 includes a body 108 and a passage 110 extending through the body 108. The passage 110 extends from an inlet 112 disposed at a proximal end 114 and extends to an outlet 116 formed at a distal end 118. An irrigation needle 120 is coupled to the irrigation portion 102 at the distal end 118.

In some implementations, a distal portion 122 of the passage 110 may have a reduced size. For example, in some instances, the distal portion 122 may have a smaller diameter cross section than a portion of the passage 110 adjacent thereto. In other instances, a size of the distal portion 122 may be continuous with an adjacent portion of the passage 110. In still other implementations, a size of the distal portion 122 may have a larger cross-sectional shape than a portion of the passage 110 adjacent thereto.

Further, in some implementations, the passage 110 may have a constant cross-section along a length of the irrigation portion 102. In other implementations, the passage 110 may have a cross-section that varies along the length of the irrigation portion 102. For example, in some instance, one or more portions of the passage 110 may have a tapered cross-section. In other instances, one or more portions of the passage 110 may have a stepped changed in cross-section. However, the passage 110 may have any desired cross-sectional provide along the length of the irrigation portion 102.

Further, in some instances, the passage 110 may have a circular cross-section. In other instances, one or more portions of the passage 110 may have a circular-cross section whereas one or more other portions of the passage 110 may have other cross-sectional shapes. Moreover, the cross-sectional profile of the passage 110 may have any desired shape.

Referring again to FIG. 3, the irrigation needle 120 may be received into the distal portion 122 of the passage 110. In some instances, the irrigation needle 120 may form an interference fit with the distal portion 122. In other instances, an adhesive may be used to attach the irrigation needle 120 within the distal portion 122. Further, in still other instances, the body 108 may be formed around the irrigation needle 120. That is, the irrigation needle 120 may be in place at the time of forming of the body 108. For example, in some instances, the body 108 may be formed by an injection molding operation. Thus, the irrigation needle 120 may be positioned at a desired location in or relative to the injection mold at the time the body 108 is molded.

The passage 110 may define a proximal portion 124 at the proximal end 114. The proximal portion 124 defines the inlet 112. As shown in the illustrated example, the proximal portion 124 has a larger cross-section than an adjacent portion of the passage 110. Thus, the proximal portion 124 may be adapted to receive an end of a conduit. For example, a portion of flexible tubing may be received into the proximal portion 124 of the passage 110. The conduit may be used to supply irrigation fluid from an irrigation fluid source.

The conduit may be removably received into the proximal portion 124 such that a passage formed by the conduit communicates with the passage 110 of the irrigation portion 102. Thus, in some instances, the conduit may form an interference fit to retain the tubing within the irrigation portion 102. In other implementations, the conduit may be permanently attached within the proximal portion 124, such as with the use of an adhesive, welding, interlocking features, or in any other desired way.

In other instances, the proximal portion 124 may have a cross-sectional shape similar to identical to an adjacent portion of passage 110. That is, in some instances, the cross-sectional shape of the proximal portion 124 is the same as or smoothly transitions into the cross-sectional shape of an adjacent portion of the passage 110. In still other implementations, the cross-sectional shape of the proximal portion 124 may have a cross-sectional shape that is smaller than an adjacent portion of the passage 110.

Thus, as shown in FIG. 3, the proximal portion 124 has a circular cross-sectional shape that defines a stepped increase in diameter over the adjacent portion of passage 110. In other cases, the passage 110 may smoothly transition into a larger diametrical size of the proximal portion 124. In other cases in which the cross-sectional shape is circular, the proximal portion 124 of the passage 110 may smoothly transition or have a constant diameter as an adjacent portion of the passage 110. Alternately, the diameter of the proximal portion 124 may be a stepped or tapered decrease compared to an adjacent portion of the passage 110.

The passage 110 of the example irrigation portion 102 includes a first portion 126 and a second portion 128. The first portion 126 has a longitudinal axis 130, and the second portion 128 has a longitudinal axis 132. An angle θ is defined by the longitudinal axes 130, 132. In some instances, the angle θ may be within the range of 0-90°. However, in other instances, the first portion 126 and the second portion 128 may be coaxial.

In the example shown, the first portion 126 includes an outlet 134. A plug 136 is disposed in the outlet 134 to prevent passage of fluid therethrough. The irrigation portion 102 is operable to direct irrigation fluid from a conduit coupled at the proximal end 114 through the passage 110, and out through the irrigation needle 120. The proximal end 114 may include one or more retaining features 115. The retaining features 115 may cooperate, for example, with a lure lock provided on a length of tubing. Thus, the retaining features 115 may be utilized to couple the irrigation portion 102 to a length of flexible tubing or other type of conduit.

Referring to FIG. 5, the irrigation portion 102 defines a longitudinally extending slot 138. As explained in more detail below, the slot 138 is configured to releasably receive a portion of the aspiration portion 104. Further, as shown in FIG. 4, the irrigation portion 102 may also include a tactile region 140. The tactile region 140 may enhance gripping of a user. In some instances, the tactile region 140 may cover a portion of an outer surface 139 of the irrigation portion 102. However, in some instances, more than one tactile region 140 may be used. In other implementations, the tactile region 140 may be eliminated.

FIGS. 6-7 show an example aspiration portion 104. Referring to FIG. 6, the aspiration portion 104 includes a body 141, a passage 142 extending through the body 141 from a proximal end 144 to a distal end 146. The aspiration portion 104 also includes a receptacle 148. The receptacle 148 is adapted to receive the irrigation portion 102. When the irrigation portion 102 is received in the receptacle 148, an outer surface 150 of the irrigation portion 102 cooperates with an inner surface 152 of the receptacle to form a seal. The seal is operable to prevent or substantially prevent fluid, such as irrigation fluid, from passing through the receptacle between the inner surface 152 and the outer surface 150 towards the proximal end 144 of the aspiration portion 104. As a result, irrigation fluid is prevented or substantially prevented from leaking out of the I/A hand piece 100. Thus, the seal allows the user to maintain a clean and dry gripping surface of the I/A hand piece 100 as well as preventing irrigation fluid from being uncontrollably released elsewhere in the environment.

Materials used to form the outer surface 150 and the inner surface 152 may be selected such that one of the materials is more malleable or pliable relative to the other. Thus, the materials may be selected such that one of materials forming the inner surface 152 or a portion thereof or the material forming the outer surface 150 or a portion thereof conforms to the other material. For example, one of the materials may be harder than the other material. Further, deformation of one of the materials relative may be an elastic deformation. In other instances, the deformation may be a plastic deformation. Thus, the materials may be selected such that compliance of one material relative to the other material forms a fluid-tight or substantially fluid-tight seal.

A portion of the distal end 146 may have a retaining feature 154 to retain the irrigation sleeve 106. For example, in some instances, the retaining feature 154 may be a threaded surface configured to cooperate with a corresponding interior threaded surface 156 of the irrigation sleeve 106 (as shown in FIG. 8). Thus, the irrigation sleeve 106 may be removably secured to the distal end 146 of the aspiration portion 104. However, other retaining features may be used to retain the irrigation sleeve 106 onto the aspiration portion 104. For example, in some instances, an annular lip formed on the distal end 146 of the aspiration portion 104 may cooperate with a lip or other feature formed on the irrigation sleeve 106 to removably retain the irrigation sleeve 106 on the aspiration portion 104. However, the disclosure is not so limited. Rather, any other suitable retaining feature may be used to removably retain the irrigation sleeve 106. The irrigation sleeve 106 may be coupled to the distal end 146 of the aspiration portion 104 when either combined with or separated from the irrigation portion 102.

The proximal end 144 may be adapted to retain a conduit thereon. For example, a conduit, such as a length of flexible tubing, may be received onto an outer surface 158 of the proximal end 144. Further, in some instances, the proximal end 144 may have a tapered shape. The conduit may be retained by an interference fit between the proximal end 144 and the conduit. In other implementations, the proximal end 144 may include retaining features to couple a conduit to the aspiration portion 104. In some instances, the retaining features include, for example, one or more raised lips, a textured surface, or any other desired feature. The proximal end 144 defines an outlet 160.

In some instances, the irrigation portion 102 and/or the aspiration portion 104 may be coupled to a surgical console. For example, the irrigation portion 102 and/or aspiration portion 104 may be coupled to a surgical console via a conduit (e.g., flexible tubing).

The passage 142 also includes a distal portion 162. In some instances, the distal portion 162 has a reduced cross-section in relation to an adjacent portion of the passage 142. For example, in some instances, the passage 142 may have a circular cross-section. Thus, the distal portion 162 may have a diametrical size smaller than an adjacent portion of the passage 142. In some instances, the size of the distal portion 162 may change gradually. For example, in some instances, the passage 142 may taper to the distal portion 162. In other instances, distal portion 162 may have an abrupt change in cross-section relative to an adjacent portion of passage 142. For example, as shown in FIG. 6, the distal portion 162 may have a stepped change in cross section.

Further, in some implementations, the passage 142 may have a constant cross-section along a length of the aspiration portion 104. In other implementations, the passage 142 may have a cross-section that varies along the length of the aspiration portion 104. For example, in some instance, one or more portions of the passage 142 may have a tapered cross-section. In other instances, one or more portions of the passage 142 may have a stepped changed in cross-section. However, the passage 142 may have any desired cross-sectional provide along the length of the aspiration portion 104.

In other instances, a size of the distal portion 162 may be continuous with an adjacent portion of the passage 142. In still other instances, a size of the distal portion 162 may be a smaller an adjacent portion of the passage 142. In some instances, the shape of the passage 142 may have a circular cross-section. In other instances, the passage 142 may have other cross-sectional shapes, such as, for example, oval, rectangular, square, pyramidal, or any other desired shape.

An aspiration needle 164 is received into the distal portion 162. In some instances, the aspiration needle 164 may form an interference fit with the distal portion 162. In other instances, an adhesive may be used to attach the aspiration needle 164 within the distal portion 162. Further, in still other instances, the body 141 may be formed around the aspiration needle 164. That is, the aspiration needle 164 may be in place at the time of forming of the body 141. For example, in some instances, the body 141 may be formed by an injection molding operation. Thus, the aspiration needle 164 may be positioned at a desired location in or relative to the injection mold at the time the body 141 is molded. In other instances, the aspiration needle 164 may be coupled to the body 141 after formation of the body 141.

The aspiration portion 104 may also include a tactile region 166. The tactile region 166 may enhance gripping of a user. In some instances, the tactile region 140 may cover a portion of an outer surface 168 of the irrigation portion 104. However, in some instances, more than one tactile region 166 may be used. In other implementations, the tactile region 166 may be eliminated.

FIG. 7 is a cross-sectional view of the aspiration portion 104 taken along line A-A. As shown, the body 141 includes a profile 170 along at least a portion of its length that is configured to be releasably received into the slot 138 formed in the irrigation portion 102. The profile 170 and slot 138 may define a form or force closure mechanism. For example, in some instances, the profile 170 and slot 138 may have a snap fit to secure the irrigation portion 102 and the aspiration portion 104 together. Thus, the irrigation portion 102 and the aspiration portion 104 may be combined by inserting the irrigation needle 120 and the distal end 118 of the irrigation portion 102 into the receptacle 148 of the aspiration portion 104 and pressing the irrigation portion 102 and the aspiration portion 104 such that the profile 170 of the aspiration portion 104 is received into the slot 138 of the irrigation portion 102.

Figure 20:
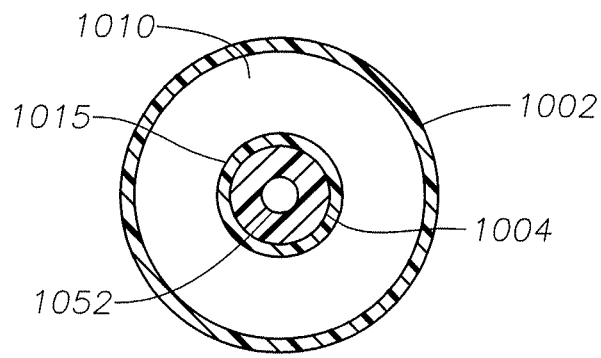
FIG. 20 is a transverse cross-sectional view of the example I/A hand piece of FIG. 10 along line D-D.

Referring to FIG. 20, the hand piece 100 may also include retaining features to maintain the irrigation portion 102 and the aspiration portion 104 in the assembled configuration. For example, in the illustrated example, a protrusion 2000 formed on the body 108 of the irrigation portion 102 is received into a recess 2002 defined by the body 141 of the aspiration portion 104. Similarly, a protrusion 2004 formed on the body 141 of the aspiration portion 104 is received into a recess 2006 defined by the body 139 of the irrigation portion 102. The protrusions 2000, 2004 and mating recesses 2002, 2006, respectively, provide for mechanical interlocking between the irrigation portion 102 and aspiration portion 104 in the assembled configuration. The protrusions 2000, 2004 and recesses 2002, 2006 are operable to couple the irrigation portion 102 and the aspiration portion 104 to each other.

The protrusions 2000, 2004 may be retained within their corresponding recesses 2002, 2006 by, for example, a snap fit. For example, once the irrigation portion 102 is received within the receptacle 148, joining forces may be applied to the irrigation portion 102 and aspiration portion 104 to force the protrusions 2000, 2004 into their respective recesses 2002, 2006. Separations forces may be applied to irrigation portion 102 and aspiration portions 104 to remove the protrusions 2000, 2004 from their respective recesses 2002, 2006. While example retaining features are described above, other retaining features may also be used. For example, different interlocking features adapted to releasably secure the irrigation portion 102 and aspiration portion 104 may be implemented.

FIGS. 8-9 show an example irrigation sleeve 106. As explained above, in some implementations, the irrigation sleeve 106 includes a threaded surface 156 and defines an interior 172. Although the irrigation sleeve 106 may include a threaded surface 156 in some implementations, in other implementations another type of retaining feature may be used. For example, the irrigation sleeve 106 may include any type of retaining operable to couple the irrigation sleeve 106 to the aspiration portion 104. Particularly, the irrigation sleeve 106 may include any suitable retaining feature operable to cooperate with the retaining feature 154 of the aspiration portion 104. The irrigation sleeve 106 may also includes ports 174. The ports 174 may be oriented 180° offset from each other about longitudinal axis 176. Although two ports 174 are shown, in other implementations, the irrigation sleeve 106 may include fewer ports, additional ports, or no ports. The irrigation sleeve 106 also includes an outlet 178. The aspiration needle 164 may extend through the outlet 178.

Referring to FIG. 2, in operation, in the assembled configuration, irrigation fluid passes from the inlet 112, through passage 110, out through the irrigation needle 120, into the irrigation sleeve 106, and out through openings 176. Irrigation fluid may also exit through the outlet 178 between the irrigation sleeve 106 and the aspiration needle 164. The combined irrigation portion 102 and aspiration portion 104 define a hand piece that may be used by a user with a single hand, thereby freeing up the user's other hand for other purposes. When separated ("separated configuration"), the irrigation portion 102 and the aspiration portion 104 may be utilized separately, for example, for use in a bimanual surgical procedure. Generally, in the separated configuration, the irrigation sleeve 106 is removed prior to use of the aspiration portion 104. However, in other instances, the irrigation sleeve 106 may remain attached during use.

FIGS. 10-21 illustrate another example I/A hand piece 1000. FIG. 10 is a cross-sectional view of the example hand piece 1000 in an assembled configuration. The hand piece 1000 includes an irrigation portion 1002, an aspiration portion 1004, and an irrigation sleeve 1006. FIGS. 11-13 show cross-sectional views of the irrigation portion 1002, the aspiration portion 1004, and the irrigation sleeve 1006 in a separated configuration.

Referring to FIGS. 11-13, the irrigation portion 1002 includes a body 1008 and a passage 1010. The passage 1010 includes an inlet 112 and an outlet 1016. The passage 1010 may extend from a proximal end 1014 to a distal end 1018. A body 1008 may define a receptacle 1015. The receptacle 1015 is configured to receive the aspiration portion 1004. As shown in FIG. 12, the outlet 1016 forms an annular ring around the receptacle.

FIG. 13 is a cross-sectional view at section B-B. FIG. 13 shows that the body 1008 may have a curved cross-sectional shape. In the illustrated example, the cross-sectional shape of the body 1008 has an arc-shape defining a recess 1020. The arc-shape is configured to receive the aspiration portion 1004, as shown, for example, in FIG. 19. Thus, in some instances, the aspiration portion 1004 nests within the recess 1020 of the irrigation portion 1002. However, the irrigation portion 1002 may have other cross-sectional shapes. For example, the irrigation portion 1002 may have any shape configured to receive the aspiration portion 1004. Further, the passage 1010 may also have a curved or arc shape. For example, the passage 1010 may have a shape that is defined by wall 1032 of the body. In other instances, though, the cross-sectional shape of the passage 1010 may define other shapes. For example, the passage 1010 may have a circular, rectangular, elliptical, pyramidal, or any other desired cross-sectional shape. Still further, a cross-sectional size and shape of the passage 1010 may also vary along a length of the irrigation portion 1002.

The proximal end 1014 may be angled relative to an adjacent portion of the body 1008. For example, an angle β may be defined between a longitudinal axis 1034 of the proximal end 1014 and a longitudinal axis 1036. In some instances, the angle β may be in the range of 90-180°. In other instances, the angle β may be 180°. That is, the longitudinal axes 1034, 1036 may be aligned.

Referring to FIG. 12, the proximal end 1014 may include one or more retaining features 1040. The retaining features 1040 may be similar to the retaining features 115, described above. Thus, retaining features 1040 may be operable to couple a conduit to the irrigation portion 1002. For example, the retaining features 1040 may cooperate with a lure lock connector attached to a piece of tubing, such as flexible tubing. In other instances, a conduit may be retained onto the proximal end 1014, for example, via an interference fit, an adhesive, gripping ribs, or in any other suitable manner.

The distal end 1018 of the body 1008 may have a retaining feature 1042. The retaining feature 1042 is operable to retain the irrigation sleeve 1006. For example, in some instances, the retaining feature 1042 may be a threaded surface configured to cooperate with a corresponding interior threaded surface 1044 of the irrigation sleeve 1006 (as shown in FIG. 17). Thus, the irrigation sleeve 1006 may be removably secured to the distal end 1018 of the irrigation portion 1002. However, other retaining features may be used to retain the irrigation sleeve 1006 onto the irrigation portion 1002. For example, in some instances, an annular lip formed on the distal end 1018 of the irrigation portion 1002 may cooperate with a lip or other feature formed on the irrigation sleeve 1006 to removably retain the irrigation sleeve 1006 on the irrigation portion 1002. However, the disclosure is not so limited. Rather, any other suitable retaining feature may be used to removably retain the irrigation sleeve 1006. The irrigation sleeve 1006 may be coupled to the distal end 1018 of the irrigation portion 1002 when either combined with or separated from the aspiration portion 1004.

FIG. 14 shows another example implementation in which the body 1008 of the irrigation portion 1002 includes a stiffening feature 1005. In some instances, the stiffening feature 1005 may be formed integrally with the body 1008. In other instances, the stiffening feature 1005 may be separate from and coupled to the body 1008. For example, the stiffening feature 1005 may be coupled to the body 1008 such as with an adhesive, interference fit, welding, cooperating interlocking features, or in any other desired manner. The irrigation sleeve 1006 is received over the stiffening feature 1005.

The irrigation sleeve 1006 and the irrigation portion 1002 may be coupled together in a manner similar to those described above. For example, the irrigation portion 1002 may include a retaining feature 1042 that is operable to retain the irrigation sleeve 1006. In some instances, the retaining feature 1042 may be a threaded surface configured to cooperate with a corresponding interior threaded surface 1044 of the irrigation sleeve 1006 (as shown in FIG. 17). However, as explained above, cooperating threaded surfaces are merely an example, and, therefore, other retaining features 1042 may be used to removably secure the irrigation sleeve 1006 to the irrigation portion 1002.

In the example shown in FIG. 14, the stiffening feature 1005 includes a plurality of freely-extending fingers 1007. The fingers 1007 may be coupled to the distal end 1018 of the body 1008. The fingers 1007 configured to flex and are, hence, compliant to a force applied thereto. The force at which the fingers 1007 may be made to flex may be adjusted to any desired force, and the rate or amount of flex at a desired force may also be adjusted to a desired level.

The fingers 1007 are received into the interior 1062 of the irrigation sleeve 1006. The fingers 1007 may be shaped to conform to the shape of the irrigation sleeve 1006. For example, the fingers 1007 may have a bent shape configured to correspond to a proximal flared portion of the irrigation sleeve 1006 and a distal elongated portion thereof. The fingers 1007 and, therefore, the stiffening feature 1005 provide increased stiffness and rigidity to the irrigation sleeve 1006. This increased stiffness and rigidity may prevent or reduce flexing or collapse of the irrigation sleeve 1006, for example, when the aspiration portion 1004 is detached from the irrigation portion 1002. As a result, the increased stiffness and rigidity provided by the stiffening feature 1005 to the irrigation sleeve 1006 provides improved performance of the irrigation portion 1002 and irrigation sleeve 1006 when used without the aspiration portion 1004. For example, during a surgical procedure in which the irrigation sleeve 1006 extends into a patient's eye, the stiffening feature 1005 may prevent collapse, twisting, or bending of the irrigation sleeve 1006 upon removal of aspiration portion 1004 or when used without the aspiration portion 1004.

FIGS. 15-16 show the aspiration portion 1004. The aspiration portion 1004 includes a body 1046, a proximal end 1048, a distal end 1050, a passage 1052, and an aspiration needle 1054. The passage 1052 may also include a distal portion 1056 that may be similar to the distal portion 162, described above. The passage 1052 defines an outlet 1058 at the proximal end 1048.

The proximal end 1048 may be adapted to retain a conduit thereon. For example, a conduit, such as a length of flexible tubing, may be received onto an outer surface 1070 of the proximal end 1048. Further, in some instances, the proximal end 1048 may have a tapered shape. The conduit may be retained by an interference fit between the proximal end 1058 and the conduit. In other implementations, the proximal end 1048 may include retaining features to couple a conduit to the aspiration portion 1004. In some instances, the retaining features include, for example, one or more raised lips, a textured surface, or any other desired feature. The proximal end 1048 defines an outlet 1058.

The aspiration needle 1054 is received into the distal portion 1056. In some instances, the aspiration needle 1054 may form an interference fit with the distal portion 1056. In other instances, an adhesive may be used to attach the aspiration needle 1054 within the distal portion 1056. Further, in still other instances, the body 1046 may be formed around the aspiration needle 1054. That is, the aspiration needle 1054 may be in place at the time of forming of the body 1046. For example, in some instances, the body 1046 may be formed by an injection molding operation. Thus, the aspiration needle 1054 may be positioned at a desired location in or relative to the injection mold at the time the body 1046 is molded. In other instances, the aspiration needle 1054 may be coupled to the body 1046 after formation of the body 1046.

Further, in some implementations, the passage 1052 may have a constant cross-section along a length of the aspiration portion 1004. FIG. 16 is a cross-sectional view of the aspiration portion 1004 taken along line C-C. As shown in FIG. 16, the passage 1052 may have a circular cross-section. The circular cross-section may be constant along the length of the passage 1052. In other implementations, the passage 1052 may have a cross-section that varies along the length of the aspiration portion 1004. For example, in some instance, one or more portions of the passage 1052 may have a tapered cross-section. In other instances, one or more portions of the passage 1052 may have a stepped changed in cross-section. However, the passage 1052 may have any desired cross-sectional provide along the length of the aspiration portion 1004. Further, a cross-sectional size and shape of the passage 1052 may vary along the length of the aspiration portion 1004.

FIG. 17 shows a cross-sectional view of the irrigation sleeve 1006. The irrigation sleeve 1006 includes an outlet 1060, an interior 1062, and the threaded surface 1044. The aspiration needle 1054 may extend through the outlet 1060. Also, although the irrigation sleeve 1006 may include a threaded surface 1044 in some implementations, in other implementations another type of retaining feature may be used. For example, the irrigation sleeve 1006 may include any type of retaining operable to couple the irrigation sleeve 1006 to the aspiration portion 1004. Particularly, the irrigation sleeve 1006 may include any suitable retaining feature operable to cooperate with the retaining feature 1042 of the aspiration portion 1004.

Referring to FIG. 18, the irrigation sleeve 1006 may also includes ports 1064. The ports 1064 may be oriented 180° offset from each other about longitudinal axis 1066. Although two ports 1064 are shown, in other implementations, the irrigation sleeve 1006 may include fewer ports, additional ports, or no ports.

Figure 19:
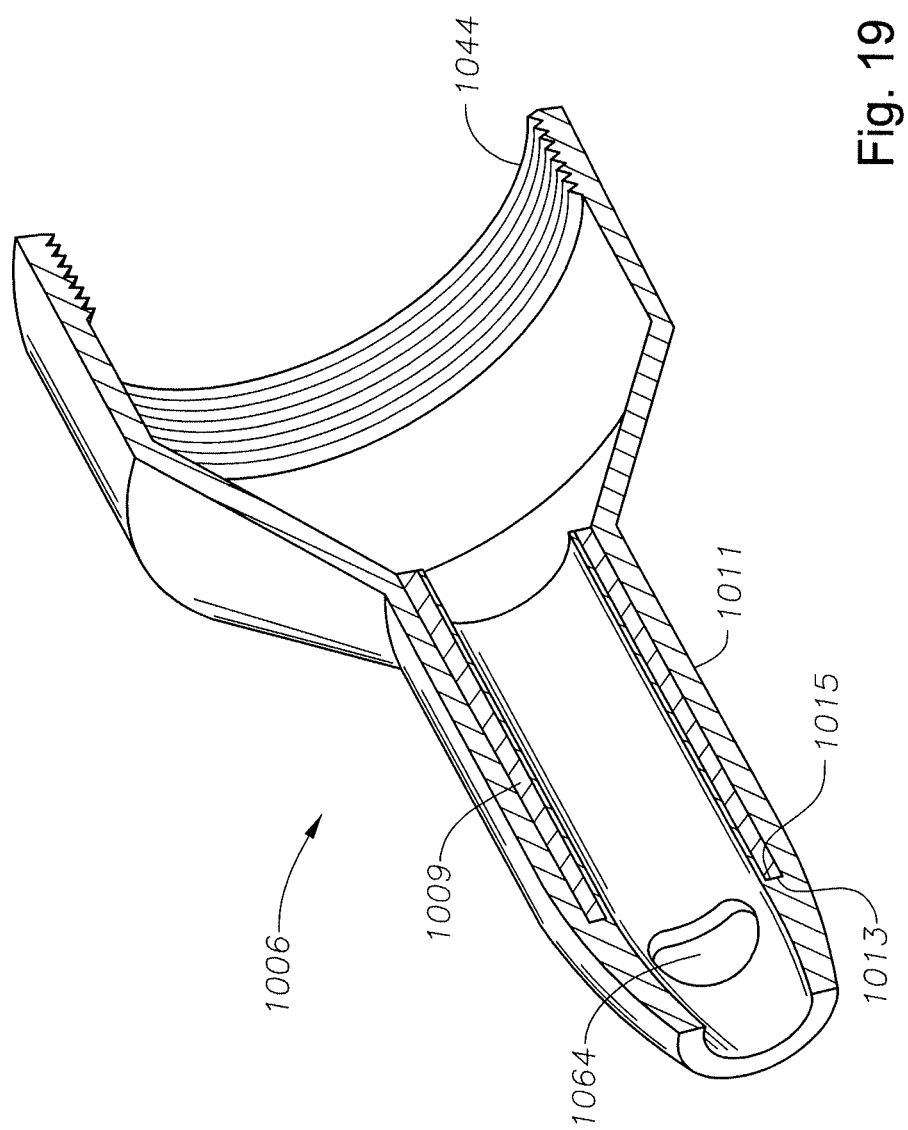
FIG. 19 is a perspective view of a cross-section of an example irrigation sleeve that includes a stiffening feature.

FIG. 19 shows another example irrigation sleeve 1006 that includes a stiffening feature 1009. The stiffening feature 1009 may be in the form of a tubular elongated member. In some instances the stiffening feature 1009 may be cylindrical in shape. In other instances, the stiffening feature 1009 may be tapered. In general, the stiffening feature 1009 may have a shape that conforms to a portion of the irrigation sleeve 1006. Further, the stiffening feature 1009 may be formed from a material having any desired stiffness. For example, in some instances, the material forming the stiffening feature 1009 may have a stiffness equal to the stiffness of the material forming the irrigation sleeve 1006. In other instances, the stiffness of the material forming the stiffening feature 1009 may be less than or greater than the material forming the irrigation sleeve 1006.

The stiffening feature 1009 may be received into an elongated portion 1011. In some instances, an outer diameter of the stiffening feature 1009 may be larger than an inner diameter of the elongated portion 1011. Thus, the stiffening feature 1009 may form an interference fit with the elongated portion 1011. In other instance, the stiffening feature may be adhered to the elongated portion 1011. For example, an adhesive may be used to attach the stiffening feature to the elongated portion 1011. In still other implementations, the stiffening feature 1009 may be embedded within the elongated portion 1011. In the implementation shown in FIG. 19, the stiffening feature 1009 is received into the elongated portion 1011, and an end 1013 abuts a shoulder 1015 formed in the elongated portion 1011.

Referring again to FIG. 10, the hand piece 1000 is shown in the assembled configuration. In the assembled configuration, the distal end 1050 of the aspiration portion 1004 is received into the receptacle 1015 of the irrigation portion 1002. The aspiration portion 1004 may be retained within the receptacle 1015, for example, by a snap fit, friction, or in any other suitable way. Thus, the aspiration portion 1004 and the irrigation portion 1002 may be releasably coupled to each other. In the assembled configuration, the aspiration needle 1054 extends through the outlet 1060 of the irrigation sleeve 1006.

Figure 21:
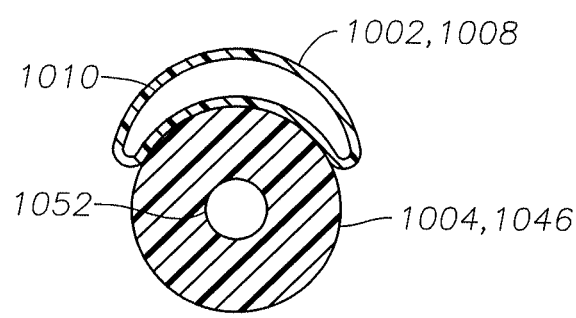
FIG. 21 is another transverse cross-sectional view of the example I/A hand piece of FIG. 10 along line E-E.
Figure 22:
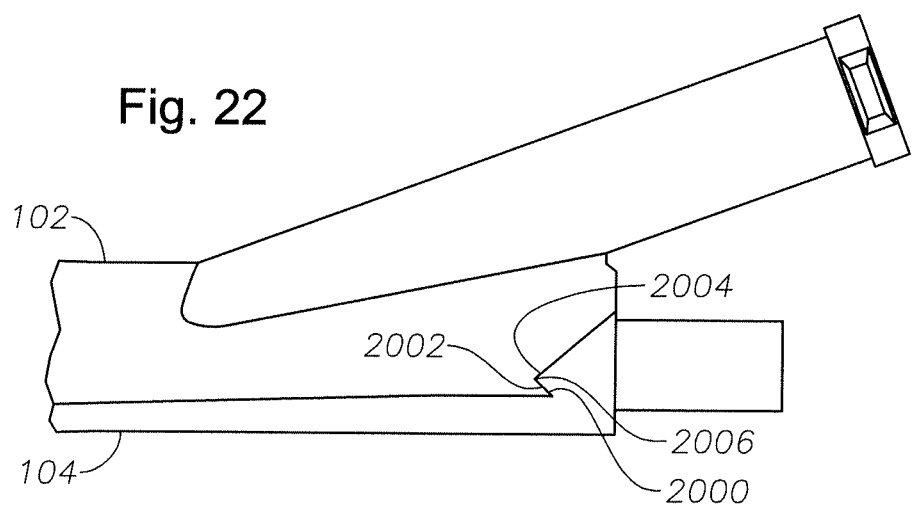
FIG. 22 is a partial detail view of the example hand piece shown in FIG. 2.

FIG. 20 is a cross-sectional view of the hand piece 1000 taken along line D-D in FIG. 10. As shown, the passage 1010 of the irrigation portion 1002 has a cross-section in the form of a ring. The passage 1052 extends through the receptacle 1015, which is encircled by the passage 1010. FIG. 21 shows a cross-sectional view of the hand piece 1000 taken along line E-E in FIG. 10. FIG. 21 illustrates that, in some implementations, the body 1046 of the aspiration portion 1004 may next within the recess 1020 defined by the body 1008 of the irrigation portion 1002.

In operation, irrigation fluid passes through the passage 1010 of the irrigation portion 1002, out through the outlet 1016, and into the interior 1062 of the irrigation sleeve 1006. The irrigation sleeve 1006 and the irrigation portion 1002 form a seal. The seal may be a fluid-tight seal that is operable to prevent or substantially prevent passage of fluid between the irrigation sleeve 1006 and the irrigation portion 1002. The irrigation fluid passes out of the irrigation sleeve 1006 through the one or more ports 1064. Additionally, irrigation fluid may exit the irrigation sleeve 1006 through the outlet 1060 between the aspiration needle 1054 and the irrigation sleeve 1006. As indicated above, the irrigation sleeve 1006 may not include ports 1064. In such implementations, the irrigation fluid may exit the irrigation sleeve 1006 through the outlet 1060.

Material may be aspirated through the aspiration needle 1054, through passage 1052, and out through outlet 1058 of the aspiration portion 1004. The aspirated material may continue through a conduit, such as flexible tubing, coupled to the aspiration portion 1004.

Thus, similar to the example shown in FIGS. 1-9, the hand piece 1000 may be used in the assembled configuration such that aspiration and irrigation functionality is provided in a single component that may be grasped in a single hand of the user. However, the hand piece 1000 may be separated into individual components, for example, for use in a bimanual surgical procedure. Further, similar to the hand piece 100, the irrigation portion 1002 and the aspiration portion 1004 may be repeatedly coupled and decoupled. For example, the irrigation portion 1002 and the aspiration portion 1004 may be coupled and decoupled numerous times during a surgical procedure, depending upon the needs or desires of the user.

Hand pieces 100 and 1000 provide many advantages. For example, hand pieces 100, 1000 provide a user with the ability to separate or combine aspiration and irrigation functionality. The user advantageously has the choice and can freely alternate hand pieces 100, 1000 between the assembled configuration and the separated configuration as desired. For example, the surgeon can place hand pieces 100, 1000 into the assembled configuration in order to have a free or unoccupied hand while performing a procedure. Alternately, the surgeon can place the hand pieces 100, 1000 into the separated configuration in order to independently place the irrigation and aspiration portions at separate locations. Further, because the irrigation portion and aspiration portion are separable, separate devices for aspiration and irrigation are not required. Thus, the hand pieces 100, 1000 provide many advantageous to a user.

While the present disclosure is illustrated by the various implementations described herein, and while the various implementations are described in detail, the scope of the present disclosure is not intended to be limited or restricted to such detail. Rather, additional advantages and modifications will readily appear to those skilled in the art. Therefore, the present disclosure in its broader aspects is not limited to the specific details, representative apparatus, and illustrative examples shown and described herein. Accordingly, departures may be made from such details without departing from the spirit or scope of the applicant's general or inventive concept. Thus, other implementations are within the scope of the following claims.

What is claimed is:

1. A surgical irrigation/aspiration system, comprising:
   a handheld irrigation portion comprising a first outer surface and having an irrigation sleeve extending from a distal end of the handheld irrigation portion, the handheld irrigation portion configured to provide an irrigation fluid to a surgical site from a surgical console; and
   a handheld aspiration portion comprising a second outer surface and having an aspiration tip extending from a distal end of the handheld aspiration portion, the handheld aspiration portion configured to provide aspiration from the surgical site;
   wherein the handheld aspiration portion is configured to be removably coupled with the handheld irrigation portion such that, when coupled:
      the aspiration tip extends through and is annularly surrounded by the irrigation sleeve and provides aspiration through a fluid outlet of the irrigation sleeve, and
      the first outer surface of the handheld irrigation portion and the second outer surface of the handheld aspiration portion define a substantially continuous outer surface along a portion of the surgical irrigation/aspiration system; and
   wherein the handheld irrigation portion is configured to provide the irrigation fluid to the surgical site and the handheld aspiration portion is configured to provide aspiration from the surgical site regardless of whether the handheld irrigation portion and handheld aspiration portion are coupled together.

2. The surgical irrigation/aspiration system of claim 1, wherein the aspiration tip extends along a central axis of the irrigation sleeve when the handheld aspiration portion is coupled with the handheld irrigation portion.

3. The surgical irrigation/aspiration system of claim 1, wherein a distal end of the aspiration tip extends beyond a distal end of the irrigation sleeve when the handheld aspiration portion is coupled with the handheld irrigation portion.

4. The surgical irrigation/aspiration system of claim 1, wherein the handheld irrigation portion comprises a receptacle configured to receive the distal end of the handheld aspiration portion when the handheld aspiration portion is coupled with the handheld irrigation portion.

5. The surgical irrigation/aspiration system of claim 4, wherein the receptacle forms a fluid-tight seal with the handheld aspiration portion when the handheld aspiration portion is coupled with the handheld irrigation portion.

6. The surgical irrigation/aspiration system of claim 4, wherein the handheld irrigation portion and the handheld aspiration portion include interlocking elements for removably coupling the distal end of the handheld aspiration portion in the receptacle of the handheld irrigation portion.

7. The surgical irrigation/aspiration system of claim 6, wherein the handheld irrigation portion interlocks with the handheld aspiration portion through a friction fit.

8. The surgical irrigation/aspiration system of claim 6, wherein the handheld irrigation portion interlocks with the handheld aspiration portion through a snap fit.

9. The surgical irrigation/aspiration system of claim 4, wherein the receptacle has a tapered portion configured to receive a cone-shaped portion of the handheld aspiration portion.

10. A surgical irrigation tool, comprising
    a handheld irrigation portion comprising a first outer surface and configured to provide an irrigation fluid to a surgical site from a surgical console; and
    an irrigation sleeve extending from a distal end of the handheld irrigation portion;
    wherein the handheld irrigation portion is configured to be removably coupled with a handheld aspiration portion comprising a second outer surface and having an aspiration tip extending from a distal end of the handheld aspiration portion, such that, when the handheld irrigation portion and handheld aspiration portion are coupled:
       the aspiration tip extends through and is annularly surrounded by the irrigation sleeve and provides aspiration from the surgical site through a fluid outlet of the irrigation sleeve, and
       the first outer surface of the handheld irrigation portion and the second outer surface of the handheld aspiration portion define a substantially continuous outer surface along a portion of the surgical instrument; and
    wherein the handheld irrigation portion is configured to provide the irrigation fluid to the surgical site regardless of whether the handheld irrigation portion and handheld aspiration portion are coupled together.

11. The surgical irrigation tool of claim 10, wherein the handheld irrigation portion comprises a receptacle configured to receive the distal end of the handheld aspiration portion when the handheld aspiration portion is coupled with the handheld irrigation portion.

12. The surgical irrigation tool of claim 11, wherein the receptacle forms a fluid-tight seal with the handheld aspiration portion when the handheld aspiration portion is coupled with the handheld irrigation portion.

13. The surgical irrigation tool of claim 11, wherein the handheld irrigation portion and the handheld aspiration portion include interlocking elements for removably coupling the distal end of the handheld aspiration portion in the receptacle of the handheld irrigation portion.

14. The surgical irrigation tool of claim 13, wherein the handheld irrigation portion interlocks with the handheld aspiration portion through a friction fit.

15. The surgical irrigation tool of claim 13, wherein the handheld irrigation portion interlocks with the handheld aspiration portion through a snap fit.

16. The surgical irrigation tool of claim 11 wherein the receptacle has a tapered portion configured to receive a cone-shaped portion of the handheld aspiration portion.

17. A surgical aspiration tool, comprising:
a handheld aspiration portion comprising a first outer surface and configured to provide aspiration from a surgical site; and
an aspiration tip extending from a distal end of the handheld aspiration portion;
wherein the handheld aspiration portion is configured to be removably coupled with a handheld irrigation portion comprising a second outer surface and having an irrigation sleeve extending from a distal end of the handheld irrigation portion, the handheld irrigation portion configured to provide an irrigation fluid to the surgical site from a surgical console, such that, when the handheld aspiration portion and handheld irrigation portion are coupled:
the aspiration tip extends through and is annularly surrounded by the irrigation sleeve and provides aspiration from the surgical site through a fluid outlet of the irrigation sleeve, and
the first outer surface of the handheld aspiration portion and the second outer surface of the handheld irrigation portion define a substantially continuous outer surface along a portion of the surgical instrument; and
wherein the handheld aspiration portion is configured to provide the aspiration from the surgical site regardless of whether the handheld irrigation portion and handheld aspiration portion are coupled together.

18. The surgical aspiration tool of claim 17, wherein the aspiration tip extends along a central axis of the irrigation sleeve when the handheld aspiration portion is coupled with the handheld irrigation portion.

19. The surgical aspiration tool of claim 17, wherein a distal end of the aspiration tip extends beyond a distal end of the irrigation sleeve when the handheld aspiration portion is coupled with the handheld irrigation portion.

* * * * *